US012659578B2

(12) United States Patent
      Huh

(10) Patent No.: US 12,659,578 B2
(45) Date of Patent: Jun. 16, 2026

(54) WELDING IMAGE PROCESSING METHOD AND DEVICE THEREFOR

(71) Applicant: OTOS WING CO., LTD., Seoul (KR)

(72) Inventor: Sung Won Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 350 days.

(21) Appl. No.: 18/225,728

(22) Filed: Jul. 25, 2023

(65) Prior Publication Data

US 2023/0370719 A1      Nov. 16, 2023

Related U.S. Application Data

(63) Continuation of application No. PCT/KR2021/006252, filed on May 20, 2021.

(30) Foreign Application Priority Data

Feb. 3, 2021    (KR) ........................ 10-2021-0015439
Mar. 24, 2021  (KR) ........................ 10-2021-0038333

(51) Int. Cl.
      *H04N 23/66*      (2023.01)
      *G01N 33/00*      (2006.01)
      *H04N 23/667*     (2023.01)
      *H04N 23/71*      (2023.01)
      *H04N 23/75*      (2023.01)

(52) U.S. Cl.
      CPC ....... *H04N 23/667* (2023.01); *G01N 33/0073* (2013.01); *H04N 23/71* (2023.01); *H04N 23/75* (2023.01)

(58) Field of Classification Search
      None
      See application file for complete search history.

(56) References Cited

U.S. PATENT DOCUMENTS

| | | | |
|---|---|---|---|
| 2006/0171704 A1 | 8/2006 | Bingle | |
| 2015/0062327 A1 | 3/2015 | Suda et al. | |
| 2015/0320601 A1* | 11/2015 | Gregg | G06T 1/0007 2/8.2 |
| 2020/0368840 A1 | 11/2020 | Huh | |
| 2020/0374510 A1 | 11/2020 | Berends | |

FOREIGN PATENT DOCUMENTS

| | | |
|---|---|---|
| JP | H11277231 A | 10/1999 |
| JP | 2005297716 A | 10/2005 |
| JP | 2018117282 A | 7/2018 |
| KR | 101673242 B1 | 11/2016 |
| KR | 101923162 B1 | 11/2018 |

* cited by examiner

*Primary Examiner* — Samira Monshi

(74) *Attorney, Agent, or Firm* — Dinsmore & Shohl LLP; Yongsok Choi, Esq.

(57) ABSTRACT

A welding image processing device and method are provided. The welding image processing device includes: a camera unit configured to capture an image of a welding portion; a cartridge arranged to be adjacent to a camera module; and a processor. The processor is configured to control a transmittance of the cartridge on the basis of a sensor value received from a sensor and acquire a welding image through the camera unit on the basis of light passing through the cartridge having the controlled transmittance.

4 Claims, 13 Drawing Sheets

<u>10</u>

WELDING IMAGE PROCESSING METHOD AND DEVICE THEREFOR

CROSS-REFERENCE TO RELATED APPLICATIONS

This application is a continuation of International Application No. PCT/KR2021/006252 filed on May 20, 2021 which claims priority to Korean Patent Application No. 10-2021-0015439 filed on Feb. 3, 2021 and Korean Patent Application No. 10-2021-0038333 filed on Mar. 24, 2021, the entire contents of which are herein incorporated by reference.

TECHNICAL FIELD

The present disclosure relates to a method of processing a welding image and a device therefor.

BACKGROUND ART

Protective gear is worn to protect a worker from light, high heat, or the like generated during a welding process such as arc welding. The worker may check only the progress of welding through the protective gear while wearing the protective gear, and thus needs to remove the protective gear and check with the naked eye to check various types of information for welding, such as conditions set in a welding device.

When the skill level of the worker is not high, in particular, when wearing an automatic welding mask or a manual welding mask, the worker may see only a portion adjacent to welding light and may not easily recognize a detailed welding situation such as a welding surrounding environment. Accordingly, it is necessary to provide the worker with a high-definition image via which the worker may visually check up to the welding surrounding environment and to provide the worker with detailed information regarding a welding portion.

In particular, when performing a welding process in which smoke is generated, it is difficult to identify a welding portion even when using welding light or illumination of a welding device.

The problems as described above may occur equally to the medical staff in skin procedures and/or medical treatment using high-luminance/high-illuminance light such as laser light as well as in welding work, and also in other work using high-luminance/high-illuminance.

DISCLOSURE

Technical Problem

The present disclosure has been made according to the above-described needs and provides a welding image processing device capable of improving the welding accuracy of a worker by showing a welding spot as well as a welding surrounding environment to the worker in a welding environment in which smoke is generated.

Embodiments of the present disclosure disclose a method of acquiring a clear welding image of a welding portion by using a camera.

The present disclosure may provide accurate information to a user in work of handling high-luminance/high-illuminance light.

However, these problems are illustrative, and the scope of the present disclosure is not limited thereby.

Technical Solution

According to an aspect of the present disclosure, a welding image processing device includes: a camera unit configured to capture an image of a welding portion; a cartridge arranged to be adjacent to a camera module; and a processor, wherein the processor is configured to: control a transmittance of the cartridge on the basis of a sensor value received from a sensor and acquire a welding image through the camera unit on the basis of light passing through the cartridge having the controlled transmittance.

According to another aspect of the present disclosure, a welding image processing method includes: receiving a sensor value from a sensor; controlling a transmittance of a cartridge on the basis of the received sensor value; and acquiring a welding image on the basis of light passing through the cartridge having the controlled transmittance.

Other aspects, features, and advantages other than those described above will become apparent from the following drawings, claims and description of the disclosure.

Advantageous Effects

A camera unit of a welding image processing device according to an embodiment of the present disclosure does not need to be implemented as a high-end camera, and thus, a manufacturing cost of the welding image processing device may be lowered and at the same time, a high-definition welding image may be acquired.

Also, the welding image processing device may control a light blocking degree or transmittance of a cartridge on the basis of an image sensor value for the welding image described above. Therefore, even when actual welding light exceeds a range of luminance or illuminance at which the camera unit may capture an image, the camera unit may generate a high-definition welding image by using light filtered by the cartridge.

DETAILED DESCRIPTION

Figure 1:
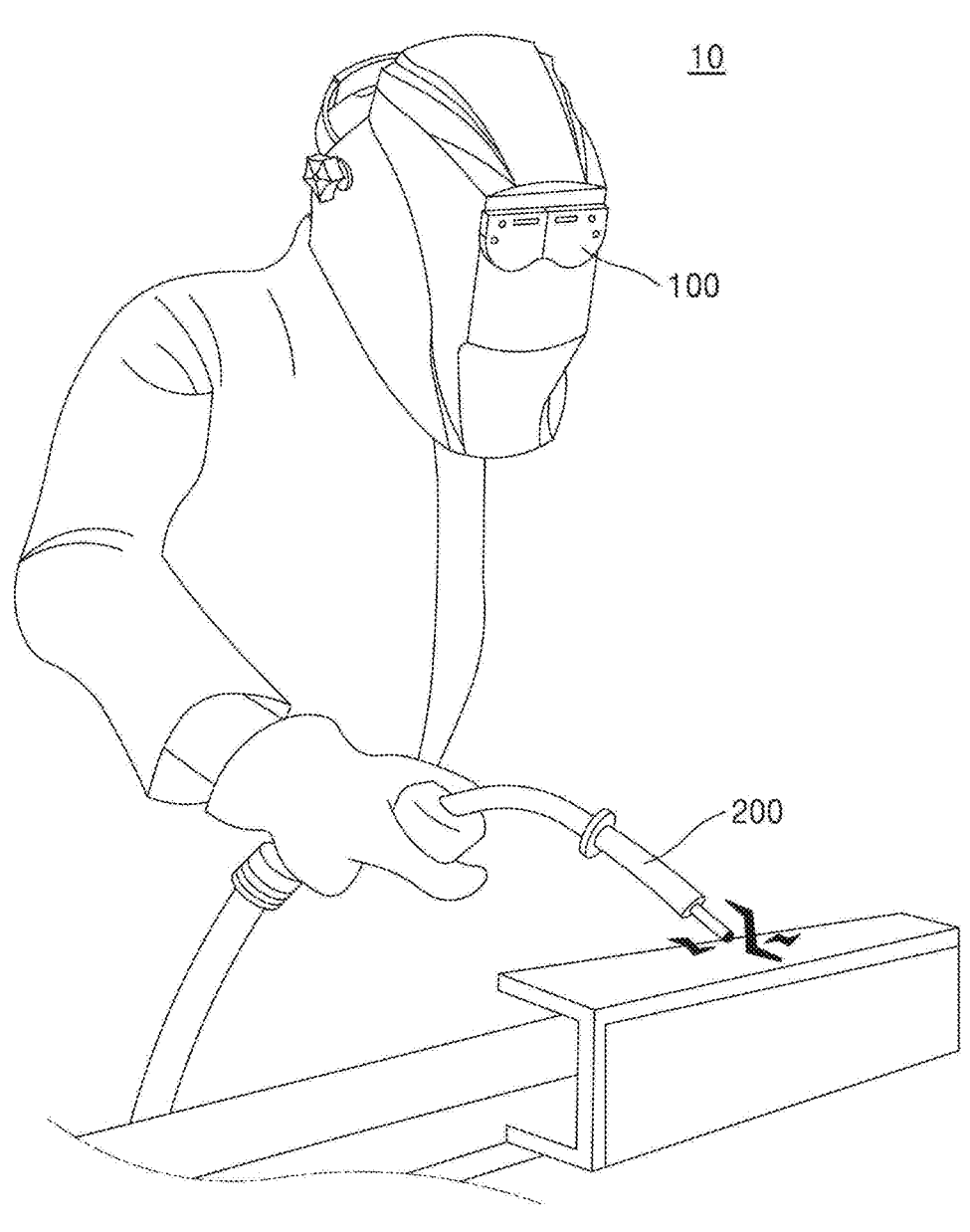
FIG. 1 is a view illustrating a structure of a welding system that performs a welding image processing method, according to an embodiment of the present disclosure.

A welding image processing device according to an aspect of the present disclosure includes: a camera unit configured to capture an image of a welding portion; a cartridge arranged to be adjacent to a camera module; and a processor, wherein the processor is configured to: control a transmittance of the cartridge on the basis of a sensor value received from a sensor; and acquire a welding image through the camera unit on the basis of light passing through the cartridge having the controlled transmittance.

MODE FOR DISCLOSURE

Hereinafter, various embodiments of the present disclosure will be described in conjunction with the accompanying drawings. Various embodiments of the present disclosure may have various changes and various embodiments, and specific embodiments are illustrated in the drawings and the related description is given. However, this is not intended to limit the various embodiments of the present disclosure to specific embodiments, and should be understood to include all changes and/or equivalents or alternatives included in the spirit and scope of the various embodiments of the present disclosure. Like reference numerals in the drawings denote like elements.

The terms "comprises", "may comprise", "includes" and/ or "may include" when used in various embodiments of the present disclosure, specify the presence of disclosed functions, operations, elements, and/or components, but do not limit additional one or more functions, operations, elements, and/or components. Also, it should be understood that the terms "comprises", "has", etc. when used in various embodiments of the present disclosure, specify the presence of stated features, integers, steps, operations, elements, and/or components, but do not preclude the presence or addition of one or more other features, integers, steps, operations, elements, components, and/or groups thereof.

Although the terms first, second, etc. may be used in various embodiments of the present disclosure may modify various components of the various embodiments, but do not limit the components. For example, the above terms do not limit the order and/or importance of corresponding components. The above terms may be used to distinguish one component from another. For example, a first user device and a second user device are both user devices and represent different user devices. For example, a first element may be termed a second element, and similarly, a second element may also be termed a first element, without departing from the scope of various embodiments of the present disclosure.

It will be understood that when an element is referred to as being "connected to" or "mounted on" another element, the element may be directly connected or coupled to the other element or intervening elements may be present. In contrast, it will be understood that when an element is referred to as being "directly connected to" or "directly mounted on" another element, there are no intervening elements present.

In embodiments of the present disclosure, the terms such as "unit", "part", etc. are terms used to refer to components that perform at least one function or operation, and these components may be implemented as hardware or software, or a combination of hardware and software. In addition, a plurality of "units", "parts", etc. may be integrated into at least one module or chip and implemented as at least one processor, except when each of them needs to be implemented as individual particular hardware.

Terms, such as those defined in commonly used dictionaries, should be interpreted as having a meaning that is consistent with their meaning in the context of the relevant art and will not be interpreted in an idealized or overly formal sense unless expressly so defined herein.

Hereinafter, various embodiments of the present disclosure will be described in detail with reference to the accompanying drawings.

FIG. 1 is a view illustrating a structure of a welding system according to an embodiment of the present disclosure.

Referring to FIG. 1, a welding system 10 according to the present disclosure may include a welding image processing device 100 and a welding torch 200. The welding image processing device 100 and the welding torch 200 may be connected to each other through a communication network to transmit and receive data to and from each other. The welding image processing device 100 and the welding torch 200 may be matched to each other on a one-to-one basis and operated, but are not limited thereto, and a one-to-n relationship is available. In other words, n welding torches 200 may be connected to one welding image processing device 100, and one welding torch 200 may be connected to n welding image processing devices 100. In addition, the welding image processing device 100 and the welding torch 200 may exchange data by communicating with a separate server (not shown).

The welding image processing device 100 may provide a worker with information regarding a welding situation. In detail, the welding image processing device 100 may acquire a welding image acquired by using at least one camera module included in a camera unit of the welding image processing device 100, generate a synthesized image on the basis of the acquired welding image, and display the synthesized image to the worker. Here, the welding image processing device 100 may generate the synthesized image by using high dynamic range (HDR) technology, and may display and provide a high-definition synthesized image and/or synthesized video to the worker. Here, the worker may visually check, via the high-definition synthesized image, information regarding a surrounding environment in addition to a shape of a welding bead and a portion adjacent to welding light.

The welding image processing device 100 according to an embodiment of the present disclosure may acquire images through the camera unit and display the respective images through at least one display unit to synthesize and provide high-definition welding images. Here, the welding image processing device 100 may synthesize images by repeatedly capturing images with different shutter speeds, ISO sensitivities, and gain values of respective cameras. The welding image processing device 100 according to an embodiment of the present disclosure may improve an image quality through contrast ratio processing on the acquired synthesized image.

Also, the welding image processing device 100 of the present disclosure may provide a function of displaying welding information in a preferred color (e.g., green or blue) by using RGB. In addition, the welding image processing device 100 of the present disclosure may provide a magnifying glass power correction function (e.g., screen enlargement and reduction). In addition, the welding image processing device 100 of the present disclosure may provide a temperature synthesis image by using a separate thermal imaging camera. Here, the welding image processing device 100 may display a welding temperature in a color. The welding image processing device 100 of the present disclosure may support a function of providing a sound (e.g., a guidance alarm) or a guidance voice for all the functions described above.

The welding torch 200 according to an embodiment of the present disclosure may detect, via at least one sensor, a welding situation for real-time welding work, including a welding temperature, a welding direction, a welding inclination, a welding speed, a distance between a base material and the welding torch 200, and the like. The welding torch 200 may monitor a state of the welding torch 200 and change a set value of torch work according to the welding situation.

The welding image processing device 100 of the present disclosure may receive information regarding work setting and a work state from the welding torch 200 through a communication network connected to the welding torch 200, and provide work information to the worker via visual feedback, on the basis of received welding information.

For example, when receiving sensing information regarding a welding temperature value, the welding image processing device 100 may output a notification corresponding to the welding temperature value in various methods such as light, vibration, and a message. Here, the notification may be visual feedback provided to the display unit or display of the welding image processing device 100, and may be auditory feedback through a sound (e.g., a guidance alarm) or a guidance voice.

Meanwhile, the sensing information regarding the welding temperature value may include information regarding whether or not the welding temperature value exceeds a preset temperature range. In addition, the sensing information regarding the welding temperature value may include a numerical value, a grade, a level, or the like corresponding to a temperature value of a welding surface.

When determining that the temperature values of the welding torch 200 and the welding surface are out of the preset temperature range, the welding image processing device 100 according to an embodiment of the present disclosure may guide the worker to stop the work. When welding is out of the preset temperature range, the quality of welding may be deteriorated, and thus, the worker may be guided to adjust the temperature value of the welding torch 200.

When detecting that a current or voltage state of the welding torch 200 is abnormal, the welding image processing device 100 according to an embodiment of the present disclosure may provide visual feedback for a warning.

Here, the visual feedback may provide an icon indicating danger in a partial region of the display unit of the welding image processing device 100, which is displaying a work site. As another example, the welding image processing device 100 may provide a work stop guide through the visual feedback by repeating an increase and a decrease in saturation of a particular color (e.g., red) on the entire screen of the display unit.

According to an embodiment of the present disclosure, the welding image processing device 100 may sense welding information via a sensor (e.g., a first sensor) included in the welding image processing device 100 in addition to at least one sensor (e.g., a second sensor) included in the welding torch 200. Here, the welding information may be acquired by detecting, via at least one sensor, the welding situation including a light level, a welding temperature, a welding direction, a welding inclination, a welding speed, a distance between a base material and the welding torch 200, and the like, which are related to the real-time welding work.

Similarly, the welding image processing device 100 may provide a guidance corresponding to the welding information, on the basis of the welding information detected via the sensor (e.g., the first sensor) included in the welding image processing device 100.

According to an embodiment of the present disclosure, after providing the guidance for stopping the work, the welding image processing device 100 may change an operation of the welding torch 200 by sensing preset motion of a user or a preset voice of the user.

In another embodiment, the welding image processing device 100 may acquire temperature values of the welding torch 200 and the welding surface through image sensing provided therein when communication with the welding torch 200 is not smooth. As an example, the welding image processing device 100 may acquire the temperature values of the welding torch 200 and the welding surface on the basis of image data acquired via the thermal imaging camera.

The above example describes only the case in which information received from the welding torch 200 is welding temperature information, and thus, the welding image processing device 100 may provide various types of guidance for various types of welding information.

Figure 2:
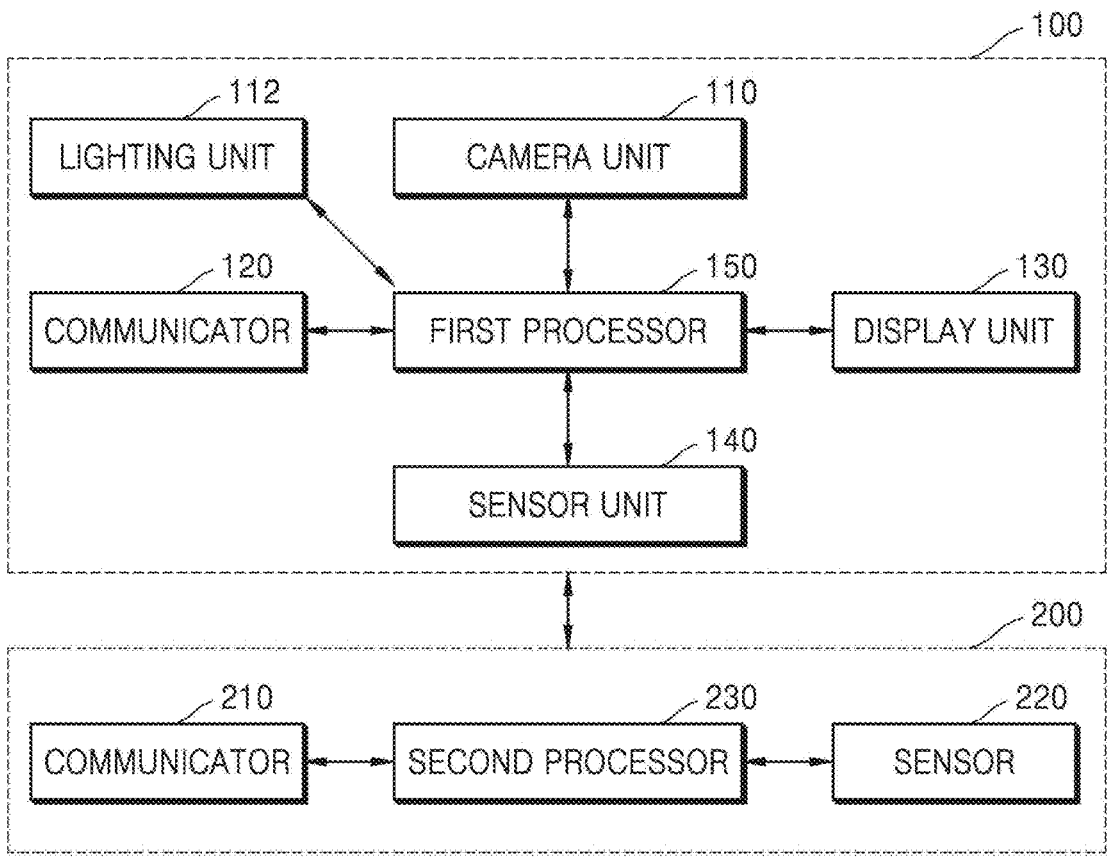
FIG. 2 is a block diagram illustrating components of a welding system according to an embodiment of the present disclosure.

FIG. 2 is a simple block diagram illustrating components of a welding system according to an embodiment of the present disclosure.

Referring to FIG. 2, a welding system 10 may include a welding image processing device 100 and a welding torch 200. The welding image processing device 100 may include a camera unit 110, a lighting unit 112, a communicator 120, a display unit 130, a first processor 150, and a sensor unit 140, and the welding torch 200 may include a communicator 210, a sensor unit 220, and a second processor 230.

The camera unit 110 may include at least one camera module, for example, the camera module may include a camera for capturing an image of a welding work site. The camera unit 110 according to an embodiment of the present disclosure may be a camera located adjacent to the display unit 130 of the welding image processing device 100. As an example, a first camera and a second camera of the camera unit 110 may be mounted symmetrically on one region of a front surface of the welding image processing device 100.

The camera unit 110 may receive a control command from the first processor 150 and capture the image of the welding work site by changing settings such as a shutter speed, ISO sensitivity, and gain in response to the control command. The camera unit 110 may include the first camera and the second camera, and the first camera and may capture the image of the welding work site through different photographing settings.

The camera unit 110 according to an embodiment of the present disclosure may be included in one region of a front portion of the display unit 130, and may have a structure in which a light-blocking cartridge is located in front of a lens that receives light from a subject.

An automatic light-blocking cartridge may block welding light generated when welding by a worker. In other words, the automatic light-blocking cartridge (not shown) may be blackened on the basis of welding light information detected via the sensor unit 140, e.g., an image sensor or a photosensor, and increase a light blocking degree of the cartridge. Here, the automatic light-blocking cartridge may include, for example, a liquid crystal display (LCD) panel of which blackening degree may be adjusted according to an alignment direction of liquid crystals. However, the automatic light-blocking cartridge is not limited thereto, and may be implemented with various panels such as a vertical align (VA) type LCD, a twist nematic (TN) type LCD, and an in plane switching (IPS) type LCD.

The blackening degree of the automatic light-blocking cartridge may be automatically adjusted according to brightness of the welding light. As described above, when automatically adjusted according to the brightness of the welding light, the sensor unit 140 may be used. When the sensor unit 140 acquires welding light information by detecting the brightness of the welding light and transmits, to the processor 150 described below, information regarding the brightness of the welding light included in the welding light information as a certain electrical signal, the first processor 150 may control the blackening degree on the basis of the brightness of the welding light.

In other words, the automatic light-blocking cartridge (not shown) may change a light blocking degree of a panel in real time to correspond to brightness of light generated from a welding surface at the welding work site, and the camera unit 110 may capture a welding image in which a certain amount of welding light is blocked by the automatic light-blocking cartridge installed on a front portion thereof.

According to an embodiment of the present disclosure, the welding image processing device 100 may not include the automatic light-locking cartridge. In this case, the user may perform welding work only with the welding image acquired via the camera unit 110.

The camera unit 110 according to an embodiment of the present disclosure may include a thermal imaging camera. The welding image processing device 100 may acquire a temperature image by synthesizing a thermal image acquired through the thermal imaging camera with an image of a welding site.

According to an embodiment of the present disclosure, the lighting unit 112, which is electrically connected to the first processor 150, may be further included. The lighting unit 112 is located outside the welding image processing device 100 and is configured to radiate light toward at least a welding work region. The lighting unit 112 may include a plurality of LED modules, and an output level of light irradiated through the lighting unit 112 may be adjusted under control of the first processor 150. According to an embodiment, the lighting unit 112 may operate in conjunction with an operation of the camera unit 110 under control of the first processor 150. A more particular embodiment is described below.

The communicator 120 is a component for receiving welding information from the welding torch 200 and transmitting a command for controlling the welding torch 200. According to an embodiment of the present disclosure, the communicator 120 may transmit a synthesized image to an external device in addition to the welding torch 200. Here, the external device may include various types of devices including a communication module such as a smart phone and a computer of a worker/third party.

The communicator 120 may be a component that performs communication with various types of external devices according to various types of communication methods. The communicator 120 may include at least one of a Wi-Fi chip, a Bluetooth chip, a wireless communication chip, and an NFC chip. In particular, when using the Wi-Fi chip or the Bluetooth chip, various types of connection information such as an SSID and a session key may be first transmitted and received, and may be used to connect communication and then transmit and receive various types of information. The wireless communication chip refers to a chip that performs communication according to various communication standards such as IEEE, Zigbee, 3rd Generation (3G), 3rd Generation Partnership Project (3GPP), and long term evolution (LTE). The NFC chip refers to a chip that operates in a fear field communication (NFC) method using a 13.56 MHz band from among various RF-ID frequency bands such as 135 kHz, 13.56 MHz, 433 MHz, 860 MHz to 960 MHz, and 2.45 GHz.

The display unit 130 is a component for providing a high-definition synthesized image to the worker. In detail, the display unit 130 may be implemented in the form of goggle glasses including a display for displaying, to the worker, a synthesized image obtained by synthesizing images acquired via the camera unit 110.

According to an embodiment of the present disclosure, a rear portion of the display unit 130, i.e., a portion facing the worker, may include a display for displaying a high-definition image to the worker, and an eyepiece and eyepiece portion for viewing the display.

The display included in the display unit 130 may display a high-definition synthesized image so that the worker may visually check a surrounding environment (e.g., a shape of a previously worked welding bead, and the like) in addition to a portion adjacent to welding light. In addition, the display unit 130 may guide the worker with visual feedback (e.g., a welding progress direction) on a welding progress state.

The display included in the display unit 130 may be implemented with various display technologies such as a liquid crystal display (LCD), organic light emitting diodes (OLED), a light-emitting diode (LED), liquid crystal on silicon (LcoS), and digital light processing (DLP). Here, the display according to an embodiment of the present disclosure may be implemented as a panel made of an opaque material, and the worker may not be directly exposed to harmful light. However, the display is not necessarily limited thereto, and may be provided as a transparent display.

The sensor unit 140 may include a plurality of sensor modules configured to detect various types of information regarding a welding site and acquire welding information. Here, the welding information may include a welding temperature, a welding direction, a welding inclination, a welding speed, a distance between a base material and a welding torch, and the like for real-time welding work. In addition, the sensor unit 140 may include an optical sensor module configured to detect a light level at least within a welding work region.

According to an embodiment of the present disclosure, the sensor unit 140 may include an illuminance sensor, and at this time, the sensor unit 140 may acquire information regarding brightness of welding light at the welding site. The sensor unit 140 may further include various types of sensors such as a proximity sensor, a noise sensor, a video sensor, an ultrasonic sensor, an RF sensor, and an optical sensor, in addition to the illuminance sensor, and may detect various changes related to a welding work environment.

The first processor 150 may synthesize welding image frames received via the camera unit 110 to generate a high-definition synthesized image. The first processor 150 may acquire a synthesized image by setting different photographing conditions of the camera unit 110 for respective frames and synthesizing frames, which are acquired in time order, in parallel. In detail, the first processor 150 may control the camera unit 110 to capture an image by changing a shutter speed, ISO sensitivity, and gain of the camera unit 110.

Here, the first processor 150 may differently set photographing conditions according to conditions such as sensed welding light at the welding site, ambient light, and the degree of movement of the welding torch 200. In detail, the first processor 150 may set the photographing conditions such that the ISO sensitivity and the gain are reduced as the welding light at the welding site and/or ambient light are higher. In addition, when detecting that the movement and/or work speed of the welding torch 200 is fast, the photographing conditions may be set to increase the shutter speed.

The first processor 150 may synthesize images having a preset number of frames in parallel. According to an embodiment of the present disclosure, respective images within preset frames may be captured under different photographing conditions.

When the number of camera units 110 is two or more, the first processor 150 according to an embodiment of the present disclosure may control the respective camera units to differently set photographing setting conditions and capture images. Even in this case, the first processor 150 may synthesize images having a preset number of frames in parallel.

In addition, the first processor 150 according to some embodiments of the present disclosure may receive a sensor value from a welding device, set a photographing mode of a camera module to a first mode or a second mode on the basis of the sensor value, and acquire an image frame of a welding portion from the camera module, i.e., may acquire an infrared image frame of the welding portion when the photographing mode of the camera module is set to the first mode.

The first processor 150 may control the overall operation of the welding image processing device 100 by using various types of programs stored in a memory (not shown). For example, the first processor 150 may include a CPU, RAM, ROM, and a system bus. Here, the ROM is a component that stores a set of commands for system booting, and the CPU copies an operating system stored in the memory of the welding image processing device 100 into the RAM according to the commands stored in the ROM, and boots a system by executing the O/S. When booting is completed, the CPU may perform various operations by copying various types of applications stored in the memory into the RAM and executing the copied applications. The first processor 150 has been described above as including only one CPU, but may be implemented with a plurality of CPUs (or DSPs, SoCs, or the like).

According to an embodiment of the present disclosure, the first processor 150 may be implemented as a digital signal processor (DSP) for processing a digital signal, a microprocessor, and/or a time controller (TCON). However, the processor 150 is not limited thereto, and may include one or more of a central processing unit (CPU), a micro controller unit (MCU), a micro processing unit (MPU), a controller, an application processor (AP) or a communication processor (CP), and an ARM processor, or may be defined as the corresponding term. In addition, the first processor 150 may be implemented as a system on chip (SoC) having a processing algorithm provided therein, or a large scale integration (LSI), or may be implemented in the form of a field programmable gate array (FPGA).

The welding torch 200 may include the communicator 210, the sensor unit 220, and the second processor 230.

The communicator 210 transmits and receives data to and from the welding image processing device 100. The communicator 210 may include a module capable of short-range wireless communication (e.g., Bluetooth, Wifi, Wifi-Direct) or long-range wireless communication (3G, high-speed downlink packet access (HSDPA) or long term evolution (LTE).

The sensor unit 220 or a second sensor is component included in the welding torch 200 to sense a welding situation such as a welding temperature, a welding speed, a welding inclination, a welding direction, and a distance between a base material and the welding torch 200.

The sensor unit 220 may detect at least one of various changes such as a change in posture of a user holding the welding torch 200, a change in roughness of a welding surface, and a change in acceleration of the welding torch 200, and may transmit, to the second processor 230, an electrical signal corresponding thereto. In other words, the sensor unit 220 may detect a state change occurring on the basis of the welding torch 200, generate a detection signal according to same, and transmit the generated detection signal to the second processor 230.

In the present disclosure, the sensor unit 220 may include various sensors, and may detect a change in state of the welding torch 200 when power is supplied to at least one preset sensor according to control during driving of the welding torch 200 (or on the basis of a user setting).

In this case, the sensor unit 220 may include at least one device from among all types of sensing devices capable of detecting a change in state of the welding torch 200. For example, the sensor unit 220 may include at least one sensor from among various sensing devices such as an acceleration sensor, a gyro sensor, an illuminance sensor, a proximity sensor, a pressure sensor, a noise sensor, a video sensor, and a gravity sensor. A light level within a welding work region, which is detected via the illuminance sensor of the welding torch 200, may be transmitted to the first processor 150 through the communicator 210, and the first processor 150 may control the lighting unit 112 and/or the camera unit 110 on the basis of the light level transmitted via the illuminance sensor of the welding torch 200 rather than the sensor unit 140 of the welding image processing device 100.

Meanwhile, the acceleration sensor is a component for sensing movement of the welding torch 200. In detail, the acceleration sensor may measure dynamic forces such as acceleration, vibration, and impact of the welding torch 200, and thus may measure the movement of the welding torch 200.

The gravity sensor is a component for detecting a direction of gravity. In other words, the result of detection by the gravity sensor may be used together with the acceleration sensor to determine the movement of the welding torch 200. In addition, a direction in which the welding torch 200 is gripped may be determined via the gravity sensor.

In addition to the types of sensors described above, the welding torch 200 may further include various types of sensors such as a gyroscope sensor, a geomagnetic sensor, an ultrasonic sensor, and an RF sensor, and may detect various changes related to the welding work environment.

Figure 3:
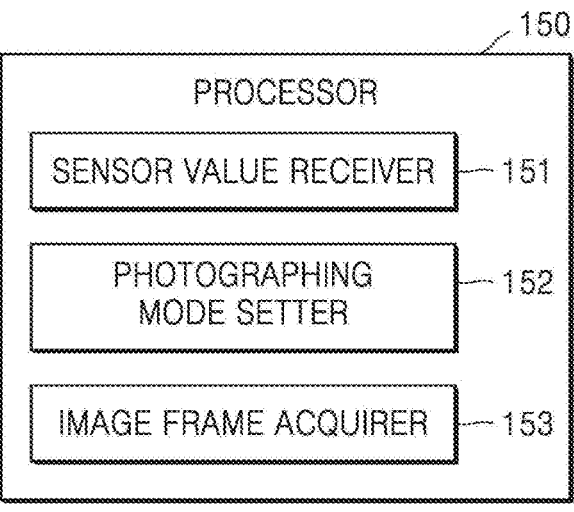
FIG. 3 illustrates an internal structure of a processor according to an embodiment of the present disclosure.

FIG. 3 illustrates an internal structure of the first processor 150 of the welding image processing device 100, according to an embodiment of the present disclosure.

The structure of the first processor 150 according to an embodiment of the present disclosure will be reviewed in detail with reference to FIG. 3. For ease of understanding, a processor described below is described as the first processor 150 of the welding image processing device 100 shown in FIG. 2. However, in an embodiment, when a welding image processing method is performed by the welding torch 200, the welding image processing method described below may be performed by the second processor 230. Also, in an embodiment, when the welding image processing method is performed by an external server, the processor described below may be a processor of an external server.

The first processor 150 of the welding image processing device 100 according to an embodiment of the present disclosure includes a sensor value receiver 151, a photographing mode setter 152, and an image frame acquirer 153. According to some embodiments, the components of the first processor 150 described above may be selectively included in or excluded from the corresponding processor. Also, according to some embodiments, the components of the processor may be separated or merged to express functions of the processor.

Figure 4:
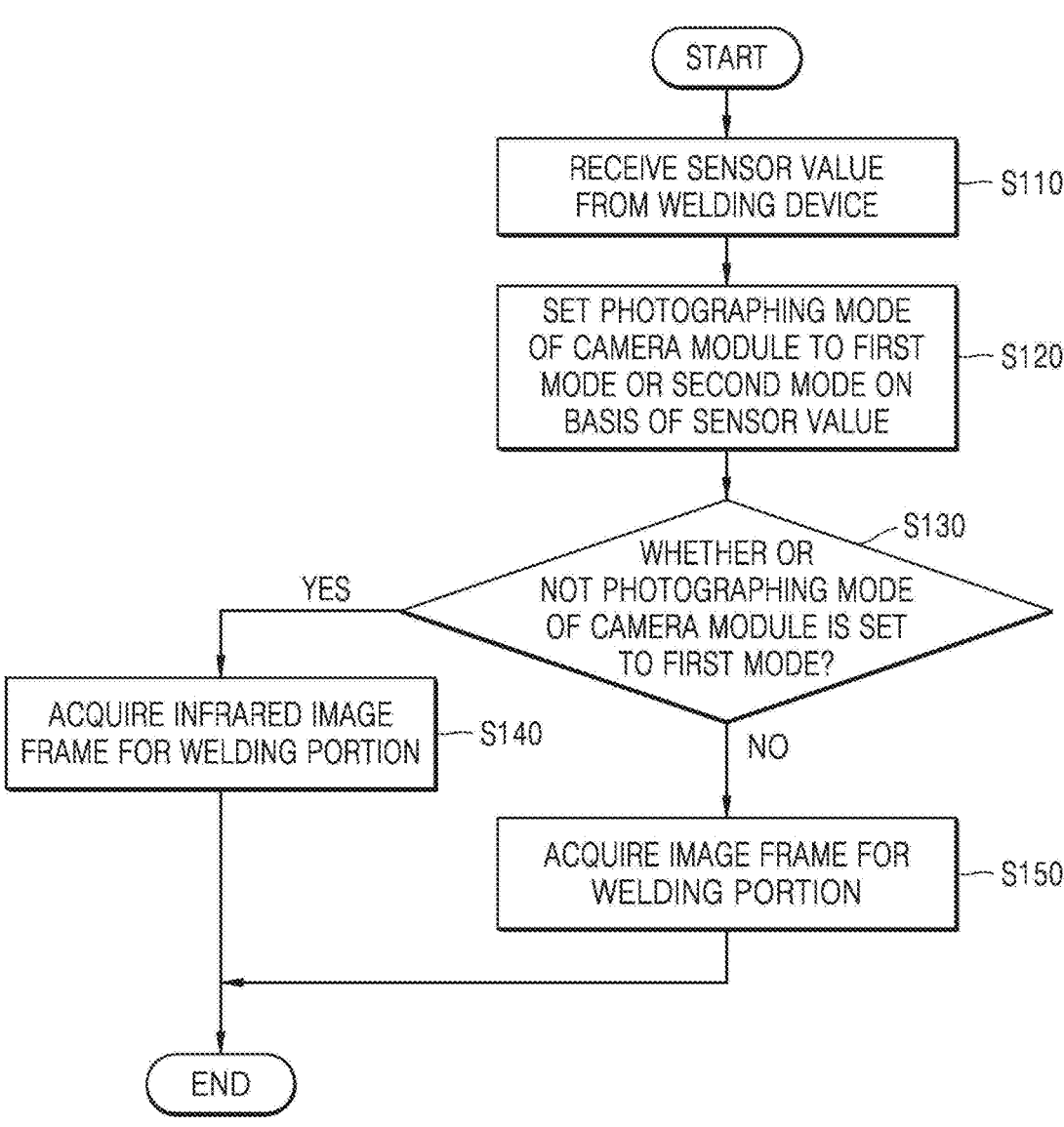
FIG. 4 is a flowchart of a welding image processing method according to an embodiment of the present disclosure.

The processor 150 and the components of the processor 150 may control a welding image processing device to perform operations S110 to S150 included in a welding image processing method of FIG. 4. For example, the processor 150 and the components of the processor 150 may be implemented to execute instructions according to a code of an operating system and a code of at least one program, which are included in a memory (not shown). Here, the components of the processor 150 may be expressions of different functions of the processor 150 that are performed by the processor 150 according to instructions provided by a program code stored in the welding image processing device 100. The internal structure and detailed operation of the processor 150 will be described with reference to the welding image processing method of FIG. 4 and embodiments of FIGS. 5 to 10.

FIG. 4 is a flowchart of a welding image processing method according to an embodiment of the present disclosure.

In operation S110, a welding image processing device may receive a sensor value from a welding device. In more detail, the welding image processing device may receive, from a smoke detection sensor, a sensor value related to the degree of smoke generation in a welding portion.

In operation S120, the welding image processing device may set, on the basis of the sensor value, a photographing mode of a camera module to a first mode or a second mode. In an embodiment, the first mode described above may be an infrared photographing mode and the second mode may be a visible ray photographing mode. In the present embodiment, the welding image processing device may transmit, to a camera, a setting signal to the first mode or the second mode.

In operation S130, the welding image processing device may check whether or not the photographing mode of the camera module is set to the first mode. The welding image processing device may set the photographing mode of the camera module to the first mode when the sensor value is greater than or equal to a threshold value, and set the photographing mode of the camera module to the second mode when the sensor value is less than the threshold value. In an embodiment, the welding image processing device may perform operation S140 when the sensor value is greater than or equal to the threshold value, and in an optional embodiment, the welding image processing device may perform operation S150 when the sensor value is less than the threshold value.

In operation S140, the welding image processing device may acquire an infrared image frame of the welding portion. In an embodiment, the welding image processing device may acquire the infrared image frame from the camera module including an infrared transmission filter when the photographing mode is set to the first mode.

In other words, a method of acquiring an infrared image frame is not limited. For example, the infrared image frame may be acquired by arranging the infrared transmission filter in front of the camera included in the welding image processing device, or the infrared image frame may be acquired through the infrared photographing mode that is electronically set.

In operation S150, the welding image processing device may acquire an image frame of the welding portion. In other words, in the present embodiment, the welding image processing device may acquire a visible ray image frame of the welding portion.

Figure 5:
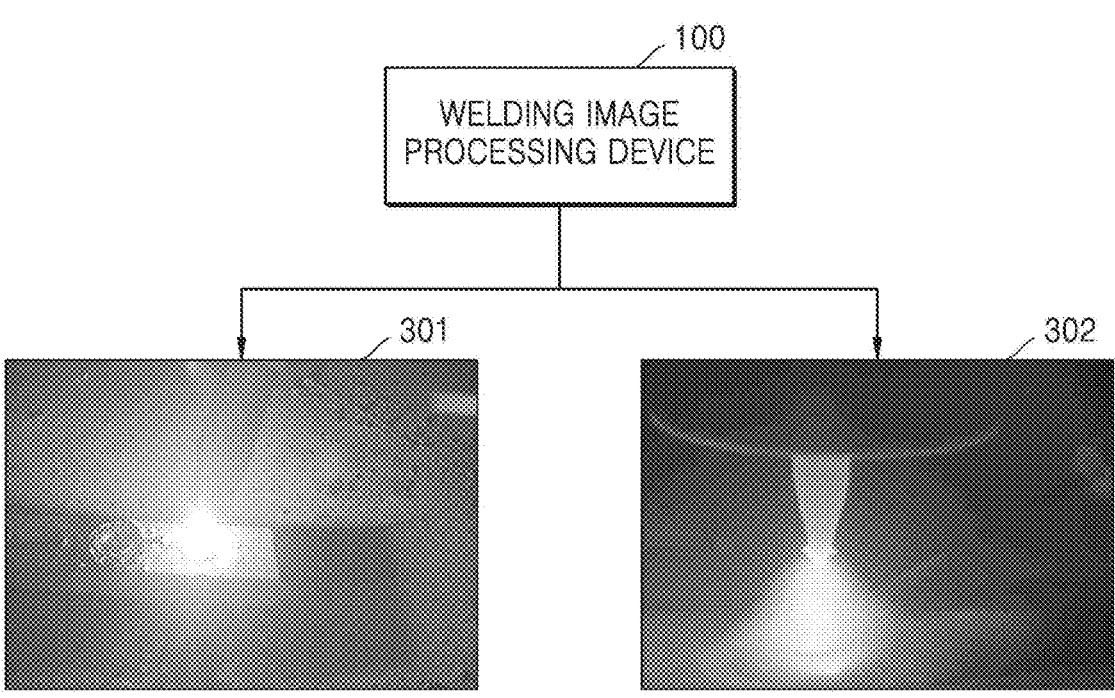
FIG. 5 is a view illustrating an image frame acquired according to a photographing mode, according to an embodiment of the present disclosure.

FIG. 5 is a view illustrating an image frame acquired according to a photographing mode, according to an embodiment of the present disclosure.

In an embodiment, a welding image processing device 100 may receive a sensor value related to the degree of smoke generation at a welding portion, and acquire a visible ray image frame 301 or an infrared image frame 302 on the basis of the sensor value described above.

In more detail, the welding image processing device 100 may set a photographing mode of a camera to a first mode or a second mode on the basis of the sensor value described above. In an embodiment, the photographing mode of the camera may be set in response to a user input of a worker performing a welding process, but according to an embodiment, the photographing mode of the camera may be set on the basis of whether or not the sensor value described above exceeds a reference value.

According to some embodiments of the present disclosure, a welding image optimized for a surrounding environment may be acquired without an additional manipulation by a user by automatically setting the photographing mode of the camera on the basis of the sensor value.

Hereinafter, a method of acquiring an infrared image frame by using an infrared transmission filter will be described in detail.

A welding image processing device may receive, from a smoke detection sensor, a sensor value related to the degree of smoke generation at a welding portion.

The welding image processing device may set a photographing mode of a camera module to a first mode when the sensor value is greater than or equal to a threshold value, and in an embodiment, the welding image processing device may acquire an infrared image frame from the camera module including an infrared transmission filter when the photographing mode is set to the first mode.

The welding image processing device according to an embodiment may acquire the infrared image frame by arranging the infrared transmission filter in front of a camera.

In other words, the welding image processing device may transmit only light in a predefined wavelength band by including a plurality of filters overlapping one another in front of the camera. For example, a camera filter may be designed so that light passes through the filter only in a wavelength band of infrared light.

For example, the infrared transmission filter may include a long pass filter and a band pass filter, but is not limited thereto.

As described above, the welding image processing device 100 may transmit only wavelengths in a predefined band by using a welding filter as described above. Accordingly, the welding image processing device 100 may acquire various optimized image frames by using various filters satisfying various criteria.

In an embodiment, the welding image processing device 100 may include a filter that satisfies a particular safety criterion. In an embodiment, the welding image processing device may include a filter that satisfies international standards for ultraviolet safety. The welding image processing device according to the present embodiment may ensure the safety of a worker by satisfying ultraviolet safety standards (CE, ANSI).

Meanwhile, a camera unit of the welding image processing device 100 may include an image sensor. Alternatively, a cartridge of the welding image processing device 100 may include a photosensor. Alternatively, the welding image processing device 100 may include both the image sensor and the photosensor. Hereinafter, as sensors included in the welding image processing device 100, the image sensor and the photosensor will be described as examples, but are not limited thereto. In other words, the welding image processing device 100 may include various types of optical sensors and may include any type of sensor which performs sensing for controlling a transmittance of the cartridge.

The welding image processing device 100 may control the transmittance of the cartridge on the basis of a sensor value of the image sensor and/or a sensor value of the photosensor. Here, an operation of controlling the transmittance of the cartridge refers to an operation of increasing or decreasing a light blocking degree by adjusting a blackening degree of the cartridge.

In general, brightness of welding light generated during welding work is higher than brightness of light (e.g., sunlight) in a normal environment. Therefore, a camera having higher specifications than a normal camera is needed to capture a welding image. Meanwhile, as the specifications of a camera increase, a price of the camera also increases, and thus, a manufacturing cost of a welding image processing device including a high-specification camera may be higher.

The welding image processing device 100 according to an embodiment of the present disclosure includes the cartridge arranged in front of a camera unit and controls the transmittance of the cartridge according to the sensor values of the image sensor and/or the photo sensor. Accordingly, the camera of the welding image processing device 100 may capture a high-quality welding image by using only a normal camera.

Accordingly, the camera unit of the welding image processing device 100 according to an embodiment of the present disclosure does not need to be implemented as a high-specification camera, and thus, a manufacturing cost of the welding image processing device 100 may be reduced, and at the same time, a high-quality welding image may be acquired.

Hereinafter, an example of the image sensor and the photosensor included in the welding image processing device 100 will be described with reference to FIG. 6.

Figure 6:
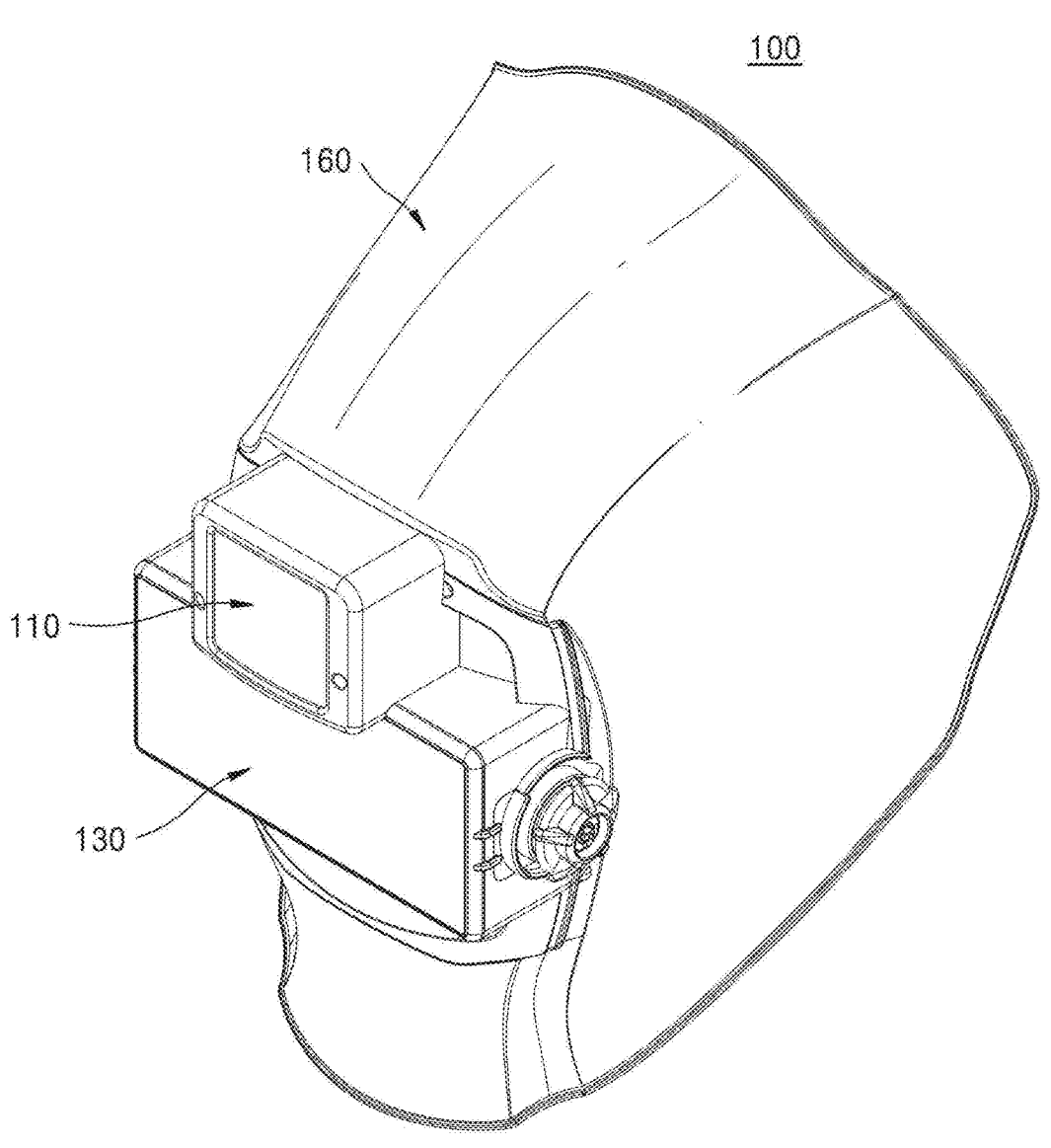
FIG. 6 is a view illustrating an example of a welding processing device according to an embodiment of the present disclosure.

FIG. 6 is a view illustrating an example of a welding processing device according to an embodiment of the present disclosure.

Referring to FIG. 6, a welding image processing device 100 includes a main body 160, a display unit 130 installed on a front surface of the main body 160, and a camera unit 110 mounted on an outer side of the main body 160. Also, although not shown in FIG. 6, as described above with reference to FIG. 2, the welding image processing device 100 may further include the lighting unit 112, the communicator 120, the sensor unit 140 and the processor 150.

The camera unit 110 may be implemented as one or more cameras. As an example, when the camera unit 110 is implemented as a single camera, the single camera may be arranged in one region of the main body 160. As another example, when the camera unit 110 is implemented as a plurality of cameras, the camera unit 110 may be symmetrically arranged in one region of the main body 160. However, a location at which the camera unit 110 is arranged on the welding image processing device 100 is not limited to a particular location. Also, when needed, the camera unit 110 may be implemented in a detachable form by changing a location thereof.

A front portion of the display unit 130 may be an external region (a region as shown in FIG. 1) corresponding to a direction in which welding work is performed. In contrast, a rear portion of the display unit 130 may be an internal region corresponding to a direction of the face of a worker.

As described above with reference to FIG. 5, the welding image processing device 100 includes a cartridge having a controllable transmittance. For example, the cartridge may be arranged on a front portion of the camera unit 110. Accordingly, light (including welding light) filtered through the cartridge may be received by the camera unit 110, and the camera unit 110 may generate a welding image according to the filtered light.

Also, as described above with reference to FIG. 5, the sensor unit 140 includes an image sensor and/or a photosensor. For example, the image sensor may be included in the camera unit 110 or may be arranged at a location adjacent to the camera unit 110. Also, the photosensor may be included in the cartridge or may be arranged at a location adjacent to the cartridge. Accordingly, the image sensor and/or the photosensor may accurately sense brightness of light at a point viewed by the camera unit 110.

Hereinafter, an example of controlling a transmittance of a cartridge on the basis of a sensor value of an image sensor or a sensor value of a photosensor will be described with reference to FIGS. 7 and 8.

Figure 7:
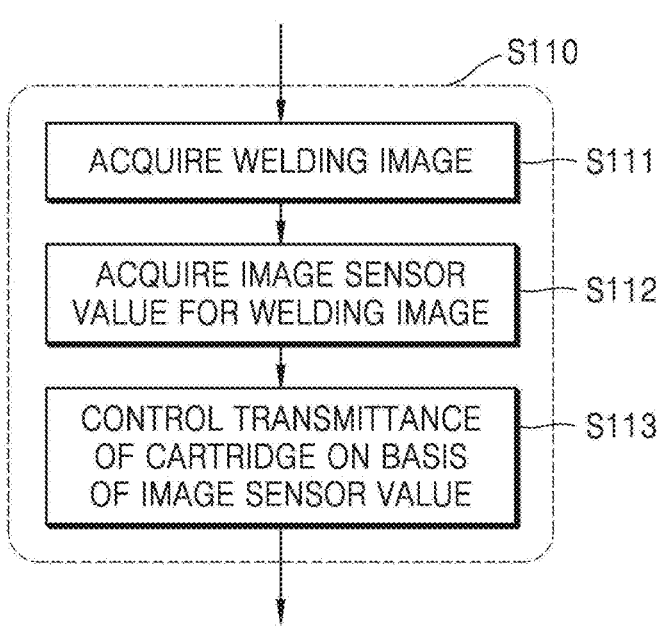
FIG. 7 is a flowchart illustrating a method of processing a welding image without a photosensor, according to an embodiment of the present disclosure.

FIG. 7 is a flowchart illustrating a method of processing a welding image without a photosensor, according to an embodiment of the present disclosure.

In operation S111, the welding image processing device 100 may acquire a welding image. In operation S112, the welding image processing device 100 may acquire a sensor value for the welding image, which is acquired from an image sensor. In operation S113, the welding image processing device 100 may control a transmittance of a cartridge on the basis of the sensor value.

According to the present embodiment, the welding image processing device 100 may control a light blocking degree or the transmittance of the cartridge on the basis of the sensor value for the welding image described above. For example, the image sensor of the welding image processing device 100 may measure brightness of welding light on the basis of the welding image. When the measured brightness of the welding light is greater than or equal to a threshold value, the welding image processing device 100 may increase the light blocking degree of the corresponding cartridge by adjusting a blackening degree of the cartridge. Therefore, even when actual welding light exceeds a luminance or illuminance range in which the camera unit 110 may capture an image, the camera unit 110 may generate a high-quality welding image by using light filtered by the cartridge.

Figure 8:
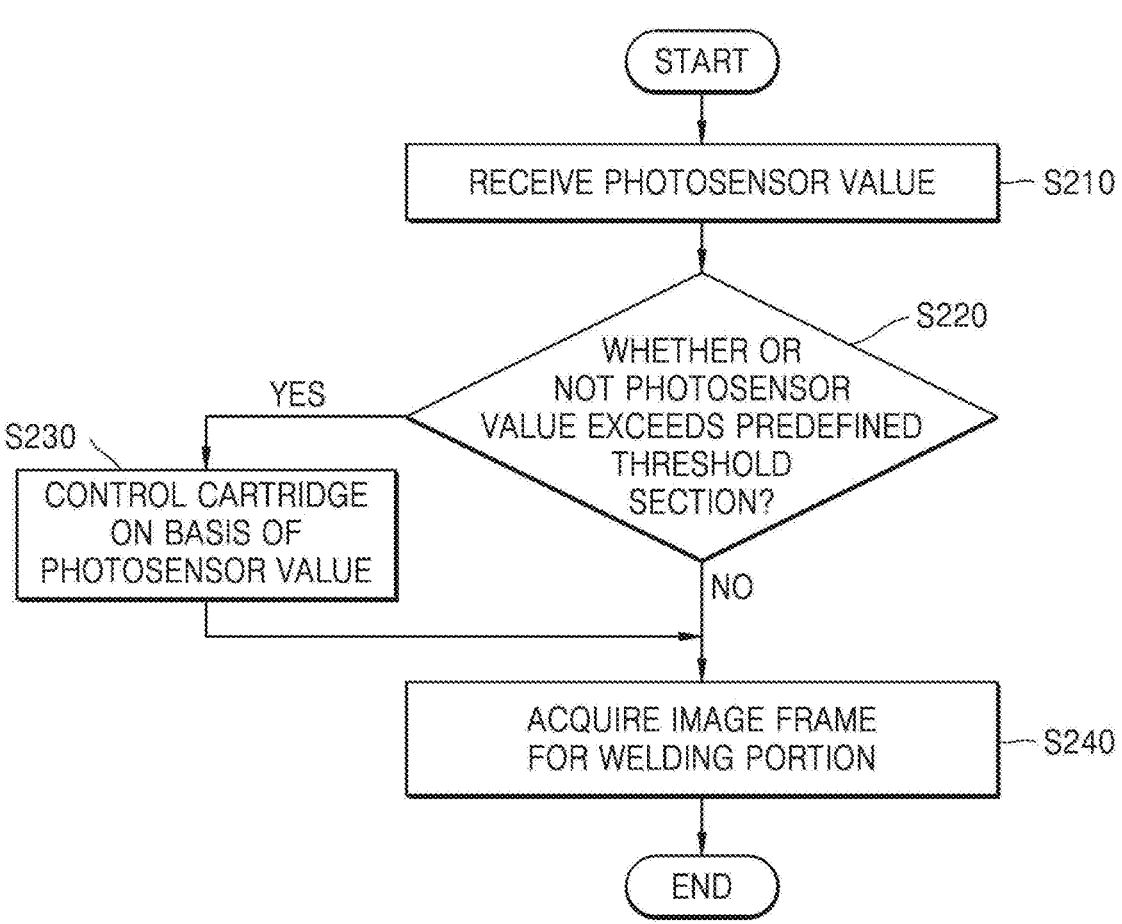
FIG. 8 is a flowchart illustrating a method of controlling a cartridge on the basis of a photosensor value, according to an embodiment of the present disclosure.

FIG. 8 is a flowchart illustrating a method of controlling a cartridge on the basis of a photosensor value, according to an embodiment of the present disclosure.

When using a neutral density filter to adjust an exposure amount of a welding camera, filters having different densities need to be used according to a situation, and the exposure amount may not be fine-tuned. The welding image processing device 100 according to an embodiment of the present disclosure may acquire an optimal welding image of a welding portion by controlling a transmittance of a cartridge on the basis of a photosensor value to adjust the exposure amount in real time.

For example, in operation S210, the welding image processing device 100 may acquire a photosensor value for a welding image being captured. In operation S220, the welding image processing device 100 may determine whether or not the photosensor value exceeds a predefined threshold section.

When the photosensor value exceeds the predefined threshold section, in operation S230, the welding image processing device 100 may control a transmittance of a cartridge on the basis of the photosensor value. Alternatively, when the photosensor value is included in the predefined threshold section, the welding image processing device 100 may not separately perform a process of controlling the transmittance of the cartridge. In operation S240, the welding image processing device 100 may acquire a welding image of a welding portion by using light filtered through the cartridge.

As described above with reference to FIGS. 7 and 8, the welding image processing device 100 may acquire an optimal welding image of a welding environment even when a low-cost camera module having a wide luminance range is used.

Meanwhile, as described above with reference to FIG. 2, the welding image processing device 100 may include an automatic light-blocking cartridge, but is not limited thereto. In other words, the welding image processing device 100 may include a plurality of filters having a preset light blocking degree, and locations of the plurality of filters may be changed according to mechanical control.

For example, the welding image processing device 100 may determine a welding environment and select one of the plurality of filters according to the welding environment. Also, the welding image processing device 100 may drive a motor that changes a location of a filter, so that the selected filter moves to a certain location.

Hereinafter, examples in which the welding image processing device 100 selects any one of a plurality of filters and controls a location of the selected filter will be described with reference to FIGS. 9 to 13.

Figure 9:
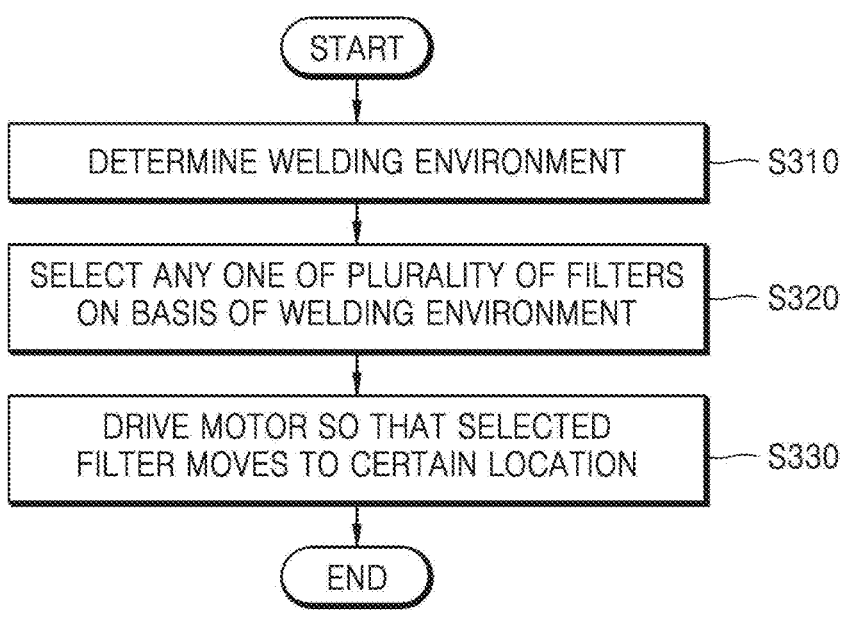
FIG. 9 is a flowchart illustrating a method by which a welding image processing device controls a location of a filter, according to an embodiment of the present disclosure.

FIG. 9 is a flowchart illustrating a method by which a welding image processing device controls a location of a filter, according to an embodiment of the present disclosure.

In operation S310, the welding image processing device 100 determines a welding environment.

The processor 150 may determine the welding environment through the sensor unit 140. For example, an optical sensor (e.g., an image sensor, a photosensor, or the like)

included in the sensor unit 140 may welding light generated while welding is performed, and the processor 150 may determine the welding environment on the basis of the detected welding light.

Here, the determining of the welding environment includes determining that welding has starts or determining that brightness of welding light changes.

When a welding arc is generated as welding starts, the sensor unit 140 may detect welding light according to the welding arc. The welding arc emits very brighter light than light in a normal environment. Accordingly, when the sensor unit 140 detects brighter light than normal light, the processor 150 may determine that the welding starts. For example, when brightness of light detected by the sensor unit 140 exceeds a certain value, the processor 150 may determine that the welding starts. However, the method by which the processor 150 determines a welding start moment is not limited to the above example.

Even while the welding is in progress, the brightness of the welding light may vary according to various conditions such as a welding temperature, a welding speed, a welding inclination, a welding direction, and a distance between a base material and a welding torch. Accordingly, the processor 150 may determine a change in brightness of the welding light according to the light detected through the sensor unit 140.

Examples in which the processor 150 determines the welding environment through the sensor unit 140 are as described above with reference to FIGS. 7 and 8.

In operation S320, the welding image processing device 100 selects any one of a plurality of filters on the basis of the welding environment. Here, each of the plurality of filters may exhibit a preset light blocking degree. In other words, a degree in which each filter transmits light (i.e., a transmittance of light) may be determined in advance. For example, a filter may be implemented by bonding an optical filter to a neutral density filter, but is not limited thereto.

As another example, a band in which the filter transmits light may be determined in advance. For example, the filter may be implemented by coating a certain material on a filter made of glass, but is not limited thereto. A band in which light passes through the filter may be determined or changed by the above coating.

The processor 150 selects, from among a plurality of filters, a filter capable of filtering welding light corresponding to a current welding environment. As described above in operation S310, the brightness of the welding light may vary according to a start of welding or a change in welding environment. Therefore, only when an appropriate filter is selected in correspondence to the brightness of the welding light, the camera unit 110 may generate a high-quality welding image by using the welding light filtered by the filter. Here, filtering the welding light by the filter indicates that a transmittance and/or transmission band of the welding light is filtered to be included in a range of luminance or illuminance at which the camera unit 110 may capture an image.

In operation S330, the welding image processing device 100 drives a motor so that the selected filter moves to a certain location.

As an example, the processor 150 may drive the motor so that the selected filter moves to the certain location due to linear movement of the plurality of filters. As another example, the processor 150 may drive the motor so that the selected filter moves to the certain location due to rotational movement of the plurality of filters. Examples in which the processor 150 moves locations of filters by driving a motor will be described below with reference to FIGS. 10 and 11.

As described above with reference to operation S320, each of the plurality of filters exhibits a preset light blocking degree, and an appropriate filter is selected from among the plurality of filters on the basis of the welding environment. In other words, a filter, which filters welding light, is selected so that a high-quality welding image is generated by the camera unit 110. Therefore, the selected filter needs to be at a location for filtering the welding light before a welding image is generated.

The processor 150 checks a current location of the selected filter. Also, the processor 150 drives the motor so that the selected filter moves to a certain location.

As an example, the certain location may be between a lens and an image sensor of the camera unit 110. As another example, the certain location may be a front surface of the lens of the camera unit 110. Examples of the certain location will be described below with reference to FIGS. 12 and 13.

Figure 10:
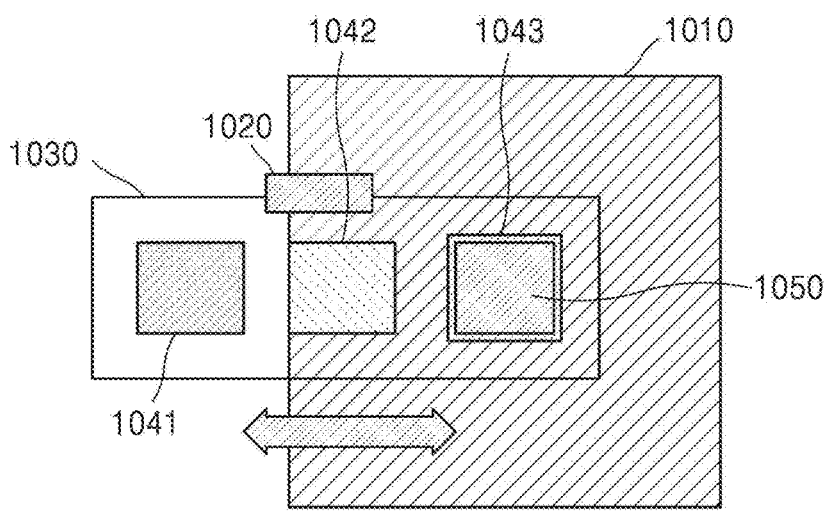
FIG. 10 is a view illustrating an example of a mechanical filter control method according to an embodiment of the present disclosure.

FIG. 10 is a view illustrating an example of a mechanical filter control method according to an embodiment of the present disclosure.

FIG. 10 illustrates some components of the welding image processing device 100. For example, the welding image processing device 100 includes a PCB 1010, a motor 1020, a filter moving unit 1030, filters 1041, 1042, and 1043, and an image sensor 1050.

Referring to FIG. 10, the filters 1041, 1042, and 1043 are arranged in series on the filter moving unit 1030. Accordingly, the processor 150 drives the motor 1020 so that the filter moving unit 1030 moves linearly (e.g., moves horizontally or moves vertically), and thus, locations of the filters 1041, 1042, and 1043 may be changed.

For example, when the processor 150 selects the filter 1043 from among the filters 1041, 1042, and 1043, the processor 150 may check a current location of the filter 1043 and drive the motor 1020 so that the filter 1043 is located on the image sensor 1050.

Meanwhile, the filter 1043 is illustrated in FIG. 10 as being located on the image sensor 1050, but is not limited thereto. Examples of a location to which the filter 1043 moves will be described below with reference to FIGS. 12 and 13.

Figure 11:
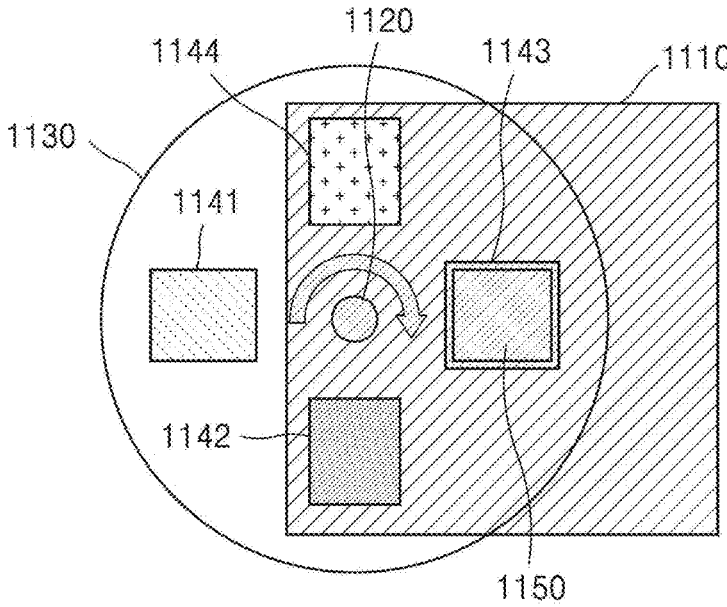
FIG. 11 is a view illustrating another example of a mechanical filter control method according to an embodiment of the present disclosure.

FIG. 11 is a view illustrating another example of a mechanical filter control method according to an embodiment of the present disclosure.

FIG. 11 illustrates some components of the welding image processing device 100. For example, the welding image processing device 100 includes a PCB 1110, a motor 1120, a filter moving unit 1130, filters 1141, 1142, 1143, and 1144, and an image sensor 1150.

Referring to FIG. 10, the filters 1141, 1142, 1143, and 1144 are circularly arranged on the filter moving unit 1130. Accordingly, the processor 150 may drive the motor 1120 so that the filter moving unit 1130 rotates, and thus, locations of the filters 1141, 1142, 1143, and 1144 may be changed.

For example, when the processor 150 selects the filter 1143 from among the filters 1141, 1142, 1143, and 1144, the processor 150 may check a current location of the filter 1143 and drive the motor 1120 so that the filter 1143 is located on the image sensor 1150.

Meanwhile, the filter 1143 is illustrated in FIG. 11 as being located on the image sensor 1150, but is not limited thereto. Examples of a location to which the filter 1143 moves will be described below with reference to FIGS. 12 and 13.

Figure 12:
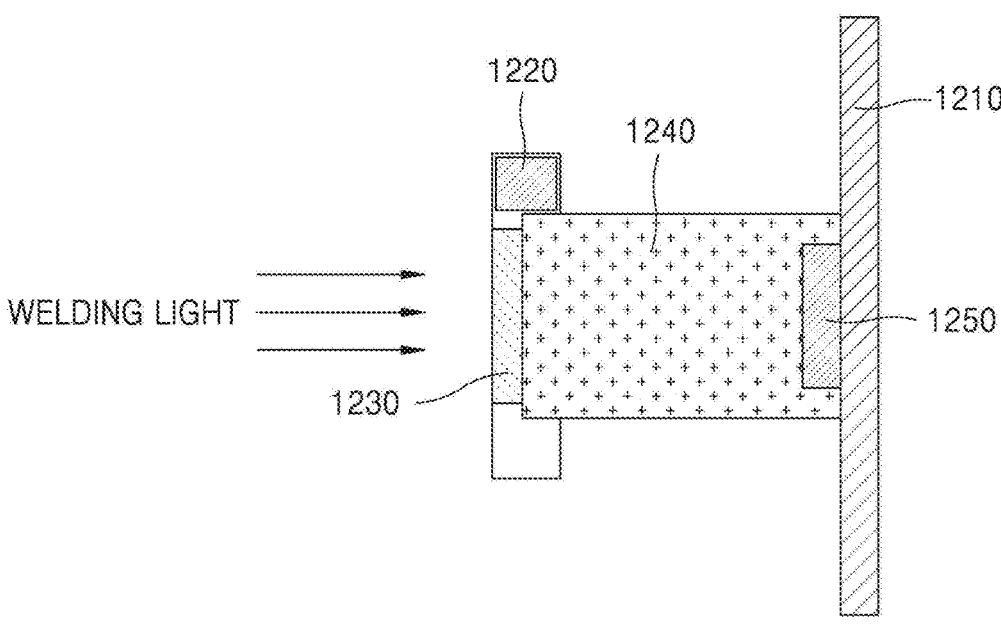
FIG. 12 is a view illustrating an example of a location to which a selected filter moves, according to an embodiment of the present disclosure.

FIG. 12 is a view illustrating an example of a location to which a selected filter moves, according to an embodiment of the present disclosure. FIG. 12 illustrates some components of the welding image processing device 100. For example, the welding image processing device 100 includes a PCB 1210, a motor 1220, a filter 1230, a lens 1240, and an image sensor 1150. The PCB 1210, the motor 1220, the filter 1230, and the image sensor 1250 shown in FIG. 12 are as shown in FIGS. 10 and 11.

The lens 1240 refers to a lens included in the camera unit 110. Also, the filter 1230 refers to a filter selected by the processor 150 from among a plurality of filters.

As described above with reference to FIGS. 9 to 11, the filter 1230 has a light blocking degree for appropriately filtering welding light, so that the camera unit 110 may generate a high-quality welding image. Accordingly, the filter 1230 needs to be moved to a location at which the camera unit 110 may generate a welding image according to the filtered welding light.

The processor 150 drives the motor 1220 to move the filter 1230 to a certain location. For example, the processor 150 may drive the motor 1220 so that the filter 1230 is located on a front surface of the lens 1240. Accordingly, the image sensor 1250 may detect light filtered by the filter 1230.

Figure 13:
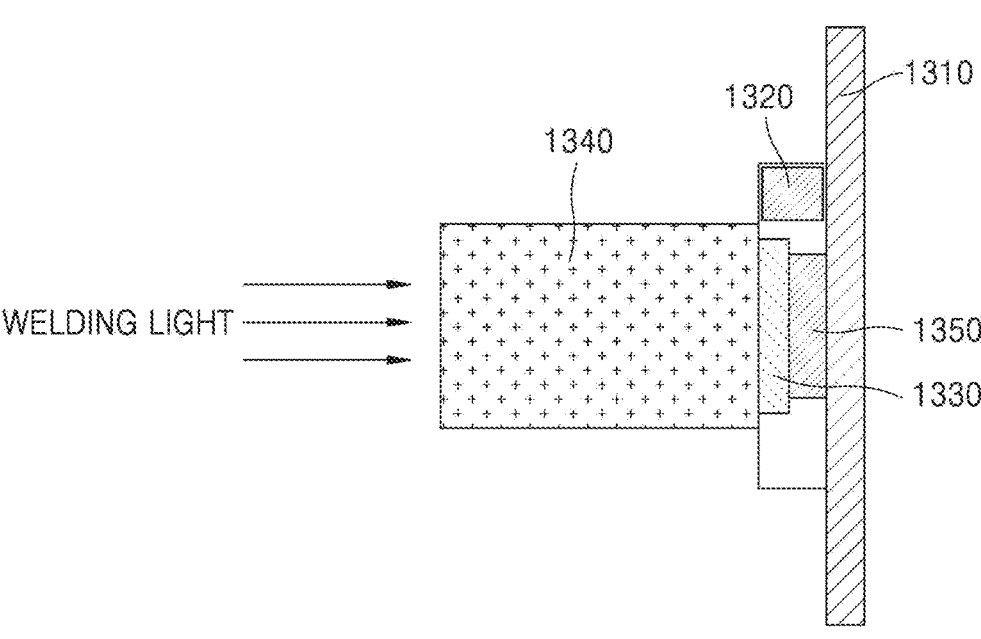
FIG. 13 is a view illustrating another example of a location to which a selected filter moves, according to an embodiment of the present disclosure.

FIG. 13 is a view illustrating another example of a location to which a selected filter moves, according to an embodiment of the present disclosure.

FIG. 13 illustrates some components of the welding image processing device 100. For example, the welding image processing device 100 includes a PCB 1310, a motor 1320, a filter 1330, a lens 1340, and an image sensor 1350. The PCB 1310, the motor 1320, the filter 1330, the lens 1340, and the image sensor 1350 illustrated in FIG. 13 are as illustrated in FIG. 12.

The processor 150 drives the motor 1320 to move the filter 1330 to a certain location. For example, the processor 150 may drive the motor 1320 so that the filter 1330 is located between the lens 1340 and the image sensor 1350. Accordingly, the image sensor 1350 may detect light filtered by the filter 1330.

All embodiments described herein may be applied in combination with each other to other embodiments.

Meanwhile, although the welding image processing device 100 according to the embodiments described above has been described as being used for welding work, the present disclosure is not necessarily limited thereto. In other words, the welding image processing device 100 according to the embodiment described above may be implemented as an information providing device, and the information providing device may be used as an information providing device for, for example, firefighting, medical, and/or skin treatment as it has the above-described structure. In other words, when performing work of irradiating high-luminance/high-illuminance light such as laser light, a user may provide an environment in which an optimal image may be acquired while reducing unneeded power consumption by adjusting an output of a lighting unit according to a situation by using the information providing device for firefighting, medical, and/or skin treatment as described above. In addition, the present disclosure may be used as an information providing device in various tasks of irradiating high-luminance/high-illuminance light.

The present disclosure has been described with reference to the embodiments shown in the drawings, but is only example, and those skilled in the art will understand that various modifications and equivalent other embodiments may be made therefrom. Therefore, the scope of the present disclosure should be defined by the spirit of appended claims.

The invention claimed is:

1. A welding image processing device comprising:

a camera unit configured to capture an image of a welding portion;

a cartridge arranged to be adjacent to a camera module; and a processor, wherein the processor is configured to:

control a transmittance of the cartridge on the basis of a sensor value received from a sensor; and acquire a welding image through the camera unit on the basis of light passing through the cartridge having the controlled transmittance, wherein the processor is configured to set, on the basis of the sensor value, a photographing mode of the camera unit to a first mode or a second mode from among a plurality of photographing modes, the first mode includes a mode for generating the welding image by using infrared light, and the second mode includes a mode for generating the welding image by using visible light.

2. The welding image processing device of claim 1, wherein the sensor includes a smoke detection sensor, and the processor is configured to set a photographing mode of the camera unit on the basis of a sensor value received from the smoke detection sensor.

3. A welding image processing method performed by a computing apparatus, the method comprising:

receiving a sensor value from a sensor;

controlling a transmittance of a cartridge on the basis of the received sensor value; and acquiring a welding image on the basis of light passing through the cartridge having the controlled transmittance, wherein the method further comprises setting, on the basis of the sensor value, a photographing mode of a camera unit to a first mode or a second mode from among a plurality of photographing modes, and wherein the first mode includes a mode for generating the welding image by using infrared light, and the second mode includes a mode for generating the welding image by using visible light.

4. The welding image processing method of claim 3, wherein the sensor includes a smoke detection sensor, and the setting includes setting the photographing mode of the camera unit on the basis of a sensor value received from the smoke detection sensor.

\* \* \* \* \*